United States Patent [19]
Des Marais

[11] 3,994,298
[45] Nov. 30, 1976

[54] FOAM AGGREGATE CATAMENIAL TAMPON

[75] Inventor: Thomas A. Des Marais, Cincinnati, Ohio

[73] Assignee: The Procter & Gamble Company, Cincinnati, Ohio

[22] Filed: Nov. 26, 1975

[21] Appl. No.: 635,458

Related U.S. Application Data

[63] Continuation-in-part of Ser. No. 543,192, Jan. 22, 1975, abandoned.

[52] U.S. Cl. .............................. 128/285; 128/270; 260/2.5 AG
[51] Int. Cl.² ........................................ A61F 13/20
[58] Field of Search ........... 128/268, 270, 285, 296, 128/156, 290; 428/315, 306; 260/2.5 AG; 427/244

[56] References Cited
UNITED STATES PATENTS

| | | |
|---|---|---|
| 3,566,871 | 3/1971 | Richter et al. ...................... 128/296 |
| 3,794,029 | 2/1974 | Dulle ................................. 128/285 |
| 3,809,088 | 5/1974 | Ulrich, Jr. ........................... 128/285 |
| 3,812,856 | 5/1974 | Duncan et al. ..................... 128/285 |
| 3,815,601 | 6/1974 | Schaefer ............................ 128/285 |
| 3,834,389 | 9/1974 | Dulle ................................. 128/285 |

OTHER PUBLICATIONS

"Detergents and Emulsifiers"–McCutchens 1967 Annual p. 264.

Primary Examiner—Aldrich F. Medbery
Attorney, Agent, or Firm—Monte D. Witte; Richard C. Witte; John V. Gorman

[57] ABSTRACT

Foams (as for example polyurethane foam) catamenial tampons which have been treated with surfactant. Catamenial tampons of this invention exhibit improved humid expansion characteristics. In a preferred embodiment, the catamenial tampons comprise particles of lubricated polyurethane foam which have been treated with surfactant and which are contained within a fluid permeable overwrap. The invention includes a process for making the above described catamenial tampons.

9 Claims, 4 Drawing Figures

FOAM AGGREGATE CATAMENIAL TAMPON

CROSS-REFERENCE TO RELATED APPLICATION

This application is a continuation-in-part of application Ser. No. 543,192, filed Jan. 22, 1975, and now abandoned.

BACKGROUND OF THE INVENTION

1. Field of the Invention

This invention relates generally to absorbent products designed to absorb body fluids and, more particularly, to catamenial receptors designed to be worn within the vagina while receiving catamenia of women and, more particularly, to improvements in tampons having an absorbent body comprising particles of absorbent foam retained as an aggregate within a suitable overwrap or sack.

2. Description of the Prior Art

Tampons of various types and descriptions are well known articles of manufacture. A major departure from prior art tampons is described and claimed in U.S. Pat. No. 3,815,601 issued June 11, 1974 to Jean E. Schaefer, said patent being assigned to the assignee of the instant invention. The Schaefer tampon comprises an absorbent body formed by an aggregate comprising separate, relatively small pieces of resilient, absorbent foam. The foam aggregate is retained within an encasing overwrap or sack having a mesh fine enough to totally contain the absorbent pieces and to prevent their penetration of the overwrap. In a preferred form of the invention, the overwrap is a relatively loose sack formed about the aggregate thereby permitting some relative movement between adjacent pieces of foam and also providing the tampon with a certain degree of flexibility. This flexibility results in a tampon which will conform to its surroundings thereby resulting in increased efficiency and wearing comfort. The tampons are usually stored in the compressed state, usually in a tubular tampon applicator.

The copending, commonly assigned application of Hutchins and Dobson, Ser. No. 506,828 filed Sept. 17, 1974, describes an improvement in the method of making the tampons described in the Schaefer patent. Generally, the method of manufacture is to produce a polyurethane foam, comminute the foam so as to provide particles of suitable size, wash and dry the comminuted foam, then volumetrically measure the amount of uncompressed foam required for each tampon and pack this volume of foam into an overwrap or sack so as to produce a tampon. The application of Hutchins and Dobson is primarily concerned with the improvement in the manufacturing process which comprises applying a small quantity of hydrophobic liquid, such as mineral oil, to the washed and dried foam thereby reducing the tendency of the particles of foam to clump with a resultant improvement in the uniformity of the quantity of foam in each tampon when made with high speed equipment and methods. While the method of Hutchins and Dobson does facilitate the manufacture of the tampons described by Schaefer, and while the resultant tampons are, in general, superior to prior art tampons, tampons made with a lightly lubricated foam exhibit reduced humid expansion, when compared to unlubricated foams, after prolonged storage in the compressed state.

Humid expansion is an important attribute of tampons. Most tampons expand rapidly when contacted with fluid, but this expansion may be too slow to prevent by-passing of the tampon by menses with associated soiling of clothing and embarrassment to the wearer. Tampons which exhibit rapid humid expansion, on the other hand, expand rapidly to conform to the interior surfaces of the vagina, even without liquid contact, thereby essentially eliminating any possibility of by-passing. The reduction in humid expansion rate after prolonged storage in the compressed state exhibited by lightly lubricated foam tampons represents an undesirable characteristic of prior art tampons.

SUMMARY OF THE INVENTION

In accordance with the present invention, lightly lubricated foam particles intended for use in catamenial tampons are treated with surfactant prior to incorporation into the tampons. The surfactant overcomes the tendency of the lubricant to reduce the humid expansion after prolonged storage in the compressed state of a tampon made from the lightly lubricated foam particles. It has also been surprisingly discovered that tampons made from lightly lubricated foam particles exhibit more rapid humid expansion after short-term storage in the compressed state than do tampons made from unlubricated foam. This humid expansion after short-term storage is still further enhanced by the incorporation of surfactant in the lubricated foam particles.

Accordingly, it is an object of this invention to provide an improved catamenial tampon comprising particles of absorbent foam retained as an aggregate by an overwrap.

It is a further object of this invention to provide an improved method of manufacturing catamenial tampons comprising particles of absorbent foam retained as an aggregate by an overwrap.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings, in which the thicknesses of some of the materials are exaggerated for clarity and in which:

DETAILED DESCRIPTION OF THE INVENTION

Figure 1:
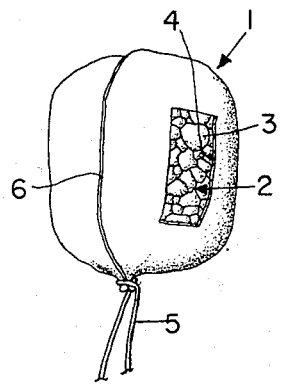
FIG. 1 is an elevation of an improved tampon of this invention with the overwrap partially cut away to permit illustration of the tampon interior.

Referring now to FIG. 1, there is shown an improved tampon 1 of this invention comprising an aggregate 2 of individual and separate particles 3 of absorbent, resilient, foam material. The aggregate 2 is wholly enclosed within the overwrap 4 and the withdrawal string 5 is securely attached to the overwrap 4. The seam by which the overwrap is joined about the aggregate is shown at 6.

Figure 2:
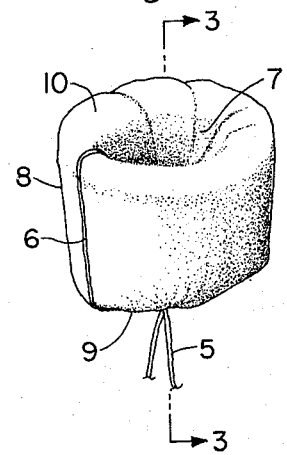
FIG. 2 is a perspective view of a rosette embodiment of the improved tampon of this invention.

FIG. 2 depicts an alternate embodiment of the improved tampon of this invention. FIG. 2 is a perspective view of a rosette tampon which has a central depending opening formed by a reentrant portion 7 as indicated. The exterior portion of the rosette configured tampon is indicated by the reference numeral 8, the cavity end is indicated by reference numeral 10, and the distal end is indicated by reference numeral 9.

Figure 3:
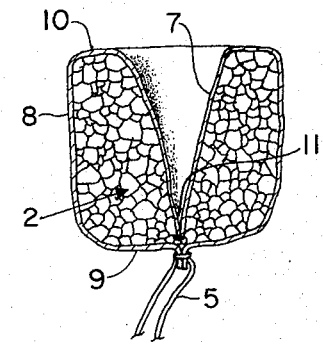
FIG. 3 is a sectional view taken along line 3—3 in FIG. 2.

FIG. 3 is a cross-sectional view of the rosette configured tampon of FIG. 2 taken along the line 3—3. This figure clearly indicates the central depending opening in the tampon formed by reentrant portion 7 terminating in the reentrant end 11. As in FIG. 1, reference numeral 2 refers to the aggregate which is wholly encased within the overwrap.

The aggregate 2 comprises individual pieces 3 of a soft, resilient, absorbent foam which has been treated as described infra. Any of numerous foam materials, as described by Schaefer, can be used. A highly preferred foam is any hydrophilic polyurethane foam material well known to those skilled in the art and is preferably made by the one-shot process. The material used as the overwrap 4 of the tampon is any soft, flexible, fluid permeable material having small apertures therethrough. While it is preferable that the overwrap be biodegradable, such a characteristic is not absolutely necessary for the practice of this invention. One particularly desirable material is a hydrophobic, spunbonded, low basis weight, polyester non-woven fabric having a measured weight of about 0.4 ounce per square yard sold under the trade name Reemay by E. I. DuPont de NeMours Company, Wilmington, Del.

While the foregoing descriptions of tampons resulting from the practice of this invention are adequate to allow one skilled in the tampon art to practice the invention with a minimum amount of extraneous experimentation, a fully detailed description of compliant tampons comprising an aggregate of separate particles of resilient, absorbent foam contained within an overwrap is given in the aforementioned U.S. Pat. No. 3,815,601 to Schaefer which is herein incorporated by reference. This patent fully describes materials suitable for use in such tampons and methods of construction of such tampons as well as alternate embodiments which can significantly benefit from the present invention.

Figure 4:
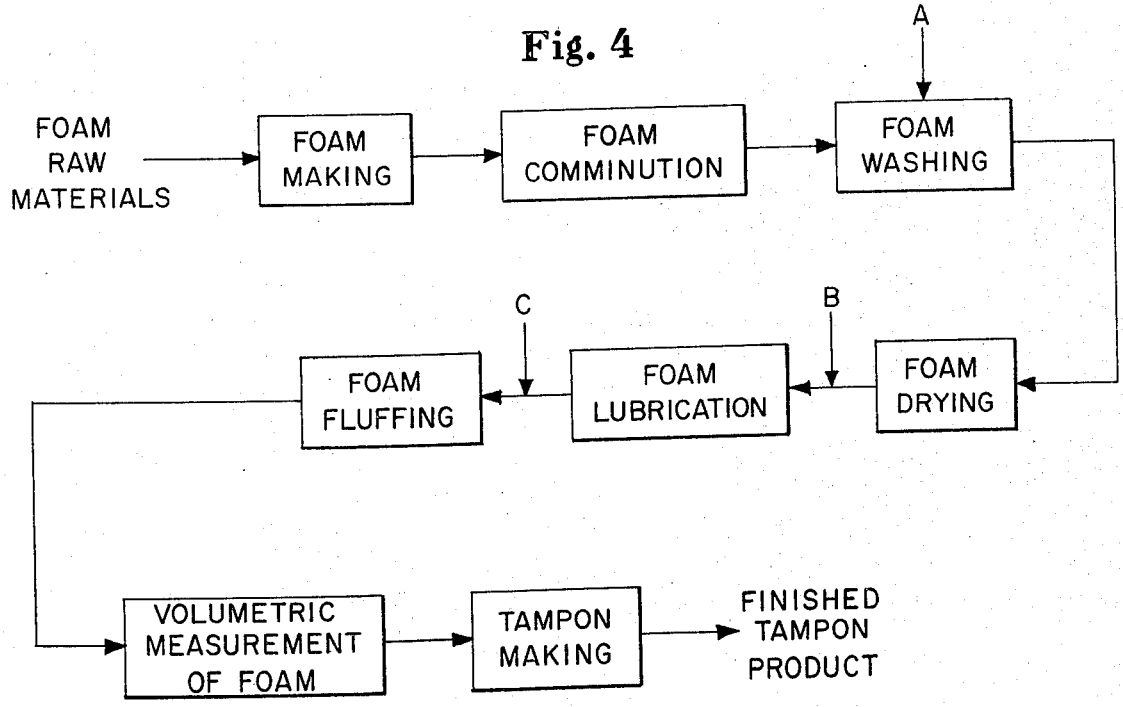
FIG. 4 is a block flow diagram of the tampon making process associated with this invention.

FIG. 4 is a block flow diagram of a tampon making process. Each step within the process can be performed by any effective means well known to those skilled in the art. Specific examples of equipment, conditions, etc., for performing each of the indicated steps is fully described in the aforementioned U.S. Pat. application Ser. No. 506,828 filed Sept. 17, 1974 by Hutchins and Dobson, which is incorporated herein by reference.

Referring now to FIG. 4, suitable raw materials such as polyol, toluene diisocyanate, catalyst, foaming surfactant, and water, all as commonly used in the one-shot polyurethane foam making process, are fed into the foam making portion of the process. The actual preparation of the polyurethane foam is described in general and in detail in the text entitled *Polyurethanes: Chemistry and Technology*, Volume 16 (in two parts) of the series entitled High Polymers by J. H. Saunders and K. C. Frisch, Interscience Publishers, 1962, which is incorporated herein by reference. After the foam is made and cured, it is sent in slabs to the Foam Comminution section of the process. Here it is comminuted by any common chopping apparatus such as the Fitzmill Guilocutter, Model 20, Code No. 28LX18D, as manufactured by the Fitzpatrick Company of Elmhurst, Ill. The foam slab is reduced to particles suitable for use in the final tampon application. For the tampons of this invention, a particle size distribution which has been found particularly suitable, expressed as fractions separated by a series of standard screens, is about 1 to about 5 percent by weight on a ⅜ inch U.S. Sieve, about 64 to about 79 percent on a No. 6 U.S. Sieve, about 15 to about 20 percent on a No. 12 U.S. Sieve, and about 5 to about 10 percent through a No. 12 U.S. Sieve.

After comminution, the foam particles are washed in a wash tank of any convenient size provided with agitation. Any suitable agitator such as a turbine blade or propellor blade agitator can be used. Those skilled in the art can readily select a suitable wash tank-agitator combination. The washing is preferably conducted at from about 70° to about 150° F (21° to 66° C) for from about 0.5 to about 25 hours, and preferably from about 1 to about 4 hours. The washed particulate foam is removed from the wash tank and sent to the Foam Drying portion of the process.

The Foam Drying portion of the process comprises means for expelling water from the washed foam, as by allowing it to drain on an open mesh screen or by passing the particles between two opposed pressure rollers, and for drying the washed foam with warmed forced air as in a drying oven. From the Foam Drying portion of the process, the washed and dried foam passes to the Foam Lubrication portion of the process. Here, liquid lubricant is added to the foam so as to reduce the tendency of the foam to clump in subsequent operations. Any suitable means of adding the lubricant to the foam may be used such as supplying the lubricant to a spray nozzle means by a positive displacement metering pump and spraying the liquid lubricant onto a bed of the dry, comminuted polyurethane foam.

After lubrication, the foam is fluffed as by a fluffer roll having a plurality of mechanical fingers secured about its periphery, said roll and fingers being contained within a closed chamber. Following fluffing, the lubricated, fluffed foam passes to the Volumetric Measurement of the Foam part of the process. The foam is processed by an apparatus such as that described in the copending commonly assigned application of Schaefer, Ser. No. 484,813, filed July 1, 1974 for Apparatus and Method for Continuously Forming and Filling Tampon Sacks, which application is hereby incorporated by reference. The particular volumetric filling apparatus utilized is, of course, largely a matter of choice of the user and depends upon the particular circumstances. As further examples, the following references describe filling apparatus of a type useful herein, said references being herein incorporated by reference: U.S. Pat. No. 2,719,661 (Eisenberg, Oct. 4, 1955); U.S. Pat. No. 2,937,670 (Eisenberg, May 24, 1960); U.S. Pat. No. 2,978,231 (Eisenberg, Apr. 4, 1961); U.S. Pat. No. 3,217,760 (Eisenberg, Nov. 16, 1955); and U.S. Pat. No. 3,298,404 (Eisenberg, Jan. 17, 1967).

After the foam is volumetrically measured, it passes to the Tampon Making portion of the process. Here, any known means including manual assembly can be used to make the Finished Tampon Product issuing from the process. Examples of tampon making procedures are described in the hereinbefore incorporated application of Schaefer and the application of Hutchins and Dobson.

As indicated in the hereinbefore incorporated application of Hutchins and Dobson, the amount of lubricant added to the particulate polyurethane foam is preferably between 0.5 percent and about 20 percent of the dry weight of particulate foam and most preferably between about 1 percent and about 5 percent. As also indicated hereinbefore, while the added lubricant improves the handling characteristics of the particulate polyurethane foam, the humid expansion rate after prolonged storage in the compressed state of tampons manufactured from this foam is somewhat reduced. The invention which forms the subject of this application overcomes this reduction in humid expansion. The humid expansion rate after short-term storage in the compressed state of tampons manufactured from this foam is further increased by this invention.

The practice of the instant invention involves the addition of surface active agents in specific amounts to the particulate polyurethane foam used in the tampons of this invention. Referring to FIG. 4, reference letters A, B, and C, indicate the points during the tampon making process at which the surface active agents can be added to the particulate polyurethane foam.

The specific surfactant used in the practice of this invention is immaterial so long as certain requirements are met. First, the surfactant must be non-toxic and non-irritating to mucus membranes. And second, the surfactant must be soluble in menses. Preferably, the surfactant is a liquid at ordinary temperatures so that its application at the preferred point in the process, as hereinafter described, is facilitated. Specific examples of suitable surface active agents are: sorbitan monolaurate, sorbitan monooleate, and sorbitan trioleate (sold under the designations Span 20, Span 80, and Span 85, respectively, by ICI America, Inc., Wilmington, Del.); and poly-oxyethylene (20) sorbitan monostereate (polysorbate 60), polyoxyethylene (20) sorbitan monooleate (polysorbate 80), polyoxyethylene (5) sorbitan monooleate, and polyoxyethylene (20) sorbitan trioleate (polysorbate 85), (sold under the designations Tween 60, Tween 80, Tween 81, and Tween 85, respectively, by ICI America, Inc.). Still other suitable surfactants are the nonionic condensates, with molecular weights greater than about 2000, of ethylene oxide and hydrophobic bases such as those formed by the condensation of propylene oxide and propylene glycol sold under the Pluronic designation by BASF Wyandotte Corp., Wyandotte, Mich.

A particularly preferred surfactant is Pluronic L-92, an A-B-A ethylene glycol-propylene glycol block copolymer of molecular weight about 3600 manufactured by BASF Wyandotte.

The quantity of surfactant added to the foam depends in some part on the critical micelle concentration of the particular surfactant. The quantity of surfactant used should be sufficient to provide a concentration in the menses absorbed into the tampon of at least the critical micelle concentration. (While the quantity of menses expected to be absorbed into a tampon varies and is dependant upon many factors such as the size of the tampon, the exact particulate polyurethane foam used in the tampon, etc., as a rule of thumb, it can be considered that weight ratio of menses to foam is approximately 10 to 1.) For most surfactants, an amount of from about 0.1 to about 15 percent by weight of the dry particulate polyurethane foam is adequate. Preferably, from 0.1 to about 5 percent of the dry weight of foam is used and most preferably from about 0.1 to about 1 percent. Depending on the specific surfactant used, excessive amounts of surfactant can tend to cause clumping of the foam and can tend to increase the risk of irritation to mucus membranes because of excessive concentration.

Preferably, the surfactant is added to the foam after the lubricant is added. This point of addition corresponds to C in FIG. 4. Means for adding the surfactant to the lubricated foam are well known to those skilled in the art and any suitable one can be used. For example, the surfactant can be sprayed onto a moving bed of the lubricated foam. In this case, the surfactant can be supplied to the spray nozzles by a metering, positive displacement pump. A Zenith Lab Metering Pump, Model No. BPB-4391-297, manufactured by Zenith Products Company of West Newton, Mass., is particularly suitable as a metering pump to supply surfactant to a Pneumatic Standard Nozzle, Series No. 1/4J, Model No. 14, manufactured by the Spraying System Company of Bellwood, Ill. As noted, it will be apparent to those skilled in the art that the selection of particular components used in the surfactant addition system is largely a matter of choice. The chief criterion is the ability of the system to produce a uniform application of surfactant to the particulate polyurethane foam.

Alternatively, the surfactant can be added to the washed and dried particulate polyurethane immediately before the Foam Lubrication step as indicated by B in FIG. 4. Equipment and procedures identical to those used in the addition of the surfactant after the lubricant addition phase of the process can be used.

A third point of foam addition is represented by A in FIG. 4. Here, the surfactant is added to the wash water in the Foam Washing step of the process. In effect, then, the comminuted foam is washed with a surfactant solution. Surfactant is left behind in the foam during the drying step. The quantity of surfactant added to the wash water can be readily calculated based on the residue desired in the foam. In a preferred process, the weight ratio of wash water to foam is 40 to 1 and the quantity of surfactant added to the wash water is 0.05 percent of the dry weight of the particulate polyurethane foam. Following the agitation of the foam in the wash water, the foam is voided of part of its water content, as by allowing it to drain or by passage between two opposed cylindrical rollers, to a weight ratio of water to foam of 3 to 1. After drying, the surfactant level on the foam is approximately 0.13 percent by weight of the dry particulate polyurethane foam.

By way of illustration, and not by way of limitation, the following examples are offered.

EXAMPLE I

A polyurethane foam was made, at 110° F (43.4° C), by the one-shot process well known in the art from the following formula: 100 parts by weight Dow SA1421 polyol (a polyether polyol of about 5000 molecular weight manufactured by the Dow Chemical Company, Midland, Mich.), 36.5 parts toluene diisocyanate, 2.8 parts water, 0.16 parts P-103 surfactant (a nonionic surfactant manufactured by BASF Wyandotte) and 0.17 parts tin octoate catalyst. After curing at room temperature for approximately 24 hours, the slab of polyurethane was comminuted to approximately the following particle size distribution: 3.6 percent by weight on a ⅜ inch mesh screen, 78.7 percent on a No. 6 U.S. Sieve, 17.7 percent through a No. 6 U.S. Sieve, and 5.6 percent through a No. 12 U.S. Sieve.

The particulate polyurethane foam was washed in distilled water for 1 hour at 70° F (21° C) with gentle agitation. 40 parts by weight water were used for each part by weight particulate polyurethane foam. The washed particulate polyurethane foam was dried in a rotating drum forced air dryer in which the entrance air temperature was 275° F (135° C).

Lubrication of the foam was accomplished by adding U.S.P. Mineral Oil in an amount equal to 1 percent by weight of the foam. The mineral oil was distributed uniformly throughout the particulate polyurethane foam mass by manual mixing.

The aforementioned Pluronic L-92 surfactant was added directly to a portion of the particulate polyurethane foam and uniformly distributed by manual mixing. Two different levels of addition of the surfactant were used on separate batches of particulate polyurethane foam: 0.1 percent and 1.0 percent by weight of the dry foam.

Tampons were made according to the teachings of Schaefer. Two grams of particulate polyurethane foam were enclosed within a Reemay overwrap and formed into rosette tampons. These tampons have an uncompressed diameter of 2.2 inches (5.6 centimeters). The tampons were compressed and packed in tubular tampon applicators having an internal diameter of 0.67 inch (1.7 centimeter). Tampons were then subjected to a humid expansion test.

In the humid expansion test, tampons contained within the tampon applicator are subjected to three cycles of the following conditioning treatment: 3 days at 80° F (26.7° C) and 80 percent relative humidity followed by 3 days at 100° F (37.8° C) and 30 percent relative humidity. After completion of the conditioning treatment, the tampons are removed from the tubular tampon applicator and subjected to 80° F (26.7° C) and 80 percent relative humidity. The diameter of the tampon is measured as it expands. From the diameter measurement, the cross-sectional area is calculated.

The 30 minute cross-sectional areas of the tampons of this Example I made from the noted foam materials are as follows: Lubricated particulate polyurethane foam without added surfactant: 0.71 square inches (4.58 square centimeters); lubricated foam containing 0.1 percent surfactant: 1.13 square inches (7.29 square centimeters); lubricated foam containing 1.0 percent surfactant: 1.65 square inches (10.62 square centimeters). As can be readily observed from the foregoing data, the humid expansion of the surfactant treated tampons is significantly and importantly greater than that of untreated tampons.

In order to more completely characterize the tampons of this Example I, a particle sink test was conducted. In the particle sink test, approximately 0.25 inch (0.63 centimeter) irregular particles of the dry polyurethane foam in question are placed on the surface of distilled water; the time required for the particles to sink, expressed in seconds, is the particle sink time. The shorter the particle sink time, the faster is the foam's absorption rate. Lubricated particulate polyurethane foam made by Example I exhibited a particle sink time of 12 hours. The lubricated particulate polyurethane foams treated with 0.1 percent and 1.0 percent surfactant exhibited particle sink times of, respectively, 12 seconds and 3.6 seconds. It is apparent that the surfactant treatment markedly improves the absorption rate of the lubricated foam tampons as well as providing the unexpected increase in humid expansion.

EXAMPLE II

Example I was repeated except that the L-92 surfactant was not added to the lubricated particulate polyurethane foam, but was added to the foam during the wash cycle. A quantity of L-92 surfactant sufficient to provide a 0.033 percent by weight concentration was added to the distilled water used in the wash. After washing, the foam was subjected to light mechanical pressure to reduce the water content to 3 parts by weight water to 1 part by weight dry particulate polyurethane foam. The foam was dried, lubricated, and made into tampons as in Example I. These tampons, which contained about 0.1 percent surfactant, exhibited a 30 minute cross-sectional area in the humid expansion test of 1.13 square inches (7.28 square centimeters). It is apparent that the surfactant can be added to the particulate polyurethane foam either during the wash cycle or after lubrication without significantly affecting the results.

EXAMPLE III

Example I was repeated with the listed variations. The distilled wash water was replaced with tap water treated by reverse osmosis. The wash temperature was 100° F (37.8° C). The washed foam was dried in a fixed bed dryer subjected to a downward flow of 300° F (149° C) air. The foam was lubricated with 1 percent by weight U.S.P. Mineral Oil sprayed onto the particulate polyurethane foam in a moving bed. Then, Pluronic L-92 surfactant was applied to the particulate polyurethane foam to a level of 0.15 percent by weight of the dry foam by placing the foam in a rotating drum 20 inches (50.8 centimeters) in diameter, rotating the drum at 30 revolutions per minute, and spraying the surfactant into the drum at a rate of 1.5 grams per minute with the use of Preval Aerosol Power Unit sprayer manufactured by the Precision Valve Corporation. Tampons made as in Example III exhibited essentially the same humid expansion characteristics as did the tampons of Example I which had been treated with 0.1 percent surfactant.

EXAMPLE IV

Example III is repeated except that the following surfactants are applied to the lubricated particulate polyurethane foam at the noted percentages of dry weight of the foam: Span 80 surfactant at 0.10 percent; Tween 60 surfactant at 1.5 percent; and Tween 81 surfactant at 5.0 percent. Essentially the same humid expansion cross-sectional areas as were obtained for 0.1 percent L-92 surfactant in Example I are obtained.

EXAMPLE V

To illustrate the surprising effect the combination of lubricant and surfactant has on the human expansion of tampons after storage in the compressed state, the following experiments were performed.

Polyurethane foam was made and comminuted as in Example I. The mass of foam particles was divided into several portions, each of which was treated with lubricant and/or surfactant at the hereinafter described levels, and tampons were made from the several portions, all as described in Example I. The tampons were then subjected to the humid expansion test after being subjected to about 5 conditioning treatment cycles and again after about 14 conditioning treatment cycles.

Lubricant and/or surfactant were added to the foam particles to make the following samples: Sample A was allowed to remain untreated (i.e., neither lubricant nor surfactant was added), Sample B was treated so as to contain 1% mineral oil, Sample C to contain 0.2% pluronic L-92 surfactant, Sample D to contain 0.5%

L-92 surfactant, Sample E to contain 1.0% L-92 surfactant, Sample F to contain 1% mineral oil and 0.2% L-92 surfactant, Sample G to contain 1% mineral oil and 0.5% L-92 surfactant, and Sample H to contain 1% mineral oil and 1% L-92 surfactant. The Table shows the results of the humid expansion test after the noted times at 80° F and 80% relative humidity.

TABLE

| Sample | % Oil | % Surfactant | Expanded Area Square Inches (5 cycles) | | | | Expanded Area Square Inches (14 cycles) | | | |
|---|---|---|---|---|---|---|---|---|---|---|
| | | | 5 min. | 15 min. | 30 min. | 60 min. | 5 min. | 15 min. | 30 min. | 60 min. |
| A | 0 | 0 | 0.47 | 0.61 | 0.70 | 0.95 | 0.47 | 0.60 | 0.69 | 0.95 |
| B | 1.0 | 0 | 0.57 | 0.68 | 0.91 | 1.54 | 0.57 | 0.67 | 0.91 | 1.54 |
| C | 0 | 0.2 | 0.47 | 0.57 | 0.68 | 1.04 | 0.47 | 0.57 | 0.67 | 1.04 |
| F | 1.0 | 0.2 | 0.61 | 0.79 | 1.13 | 1.89 | 0.60 | 0.78 | 1.13 | 1.89 |
| D | 0 | 0.5 | 0.61 | 0.71 | 1.09 | 2.08 | 0.60 | 0.71 | 1.08 | 2.07 |
| G | 1.0 | 0.5 | 0.79 | 1.45 | 2.16 | 2.48 | 0.78 | 1.43 | 2.14 | 2.47 |
| E | 0 | 1.0 | 1.04 | 2.08 | 2.62 | 2.92 | 1.04 | 2.07 | 2.61 | 2.91 |
| H | 1.0 | 1.0 | 1.33 | 2.16 | 2.63 | 3.0 | 1.33 | 2.14 | 2.61 | 2.99 |

From the data in the Table, it is apparent that a low level of lubricant improves the humid expansion characteristics of foam tampons after short-term storage in the compressed state. The data further indicate that the addition of surfactant to the foam prior to compression increases the humid expansion ability of tampons made from the foam. Surprisingly, it can be seen from the data that the combination of mineral oil and surfactant further improves the humid expansion of the tampons.

As noted in the preceding examples, the humid expansion of tampons made from lubricated particulate polyurethane foam treated by the process of this invention is improved. Enhanced wicking rates and particle sink times, which generally measure the ability of the tampon to rapidly absorb menses, are auxilliary benefits in addition to the unexpected increase in humid expansion.

While this invention has been described in terms of catamenial tampons comprising particulate polyurethane foam, it will be apparent to those skilled in the art that the teachings herein can be readily extended to include fluid receptor products other than catamenial tampons and materials other than particulate polyurethane foams. For example, solid polyurethane foam tampons and polyurethane foam-containing tampons made according to the teachings of Dulle in U.S. Pat. No. 3,794,029 (Feb. 26, 1974) and U.S. Pat. No. 3,843,389 (Sept. 10, 1974), both incorporated herein by reference, can benefit from the practice of this invention. Other products in which the practice of the instant invention can be useful include fluid receptors such as sanitary napkins, incontinent pads, diapers, bandages, and the like.

What is claimed is:

1. A catamenial tampon with improved humid expansion characteristics comprising a resilient, absorbent, particulate lubricated foam material treated with non-ionic surfactant.

2. The catamenial tampon of claim 1 wherein said surfactant is present at from about 0.1 to about 15 percent by weight of said foam material.

3. The catamenial tampon of claim 1, wherein said surfactant is present at from about 0.1 to about 5 percent by weight of said foam material.

4. A catamenial tampon with improved humid expansion characteristics comprising resilient, absorbent, lubricated foam material in particulate form contained within a permeable overwrap, said foam material having been treated with non-ionic surfactant.

5. The catamenial tampon of claim 4, wherein said foam material is polyurethane.

6. The catamenial tampon of claim 5, wherein said surfactant is present at from about 0.1 to about 15 percent.

7. The catamenial tampon of claim 5, wherein said surfactant is present at from about 0.1 to about 5 percent by weight of said foam material.

8. The catamenial tampon of claim 4, wherein said surfactant is present at from about 0.1 to about 15 percent by weight of said foam material.

9. The catamenial tampon of claim 4, wherein said surfactant is present at from about 0.1 to about 5 percent by weight of said foam material.

* * * * *